United States Patent
Landi et al.

(10) Patent No.: US 6,829,500 B2
(45) Date of Patent: Dec. 7, 2004

(54) METHOD AND DEVICE FOR DETERMINING ACCESS TO A SUBSURFACE TARGET

(75) Inventors: Michael K. Landi, Kenmore, NY (US); Walter Grand, Buffalo, NY (US)

(73) Assignee: Minrad Inc., Buffalo, NY (US)

( * ) Notice: Subject to any disclaimer, the term of this patent is extended or adjusted under 35 U.S.C. 154(b) by 0 days.

(21) Appl. No.: 09/333,251

(22) Filed: Jun. 15, 1999

(65) Prior Publication Data

US 2003/0036692 A1 Feb. 20, 2003

Related U.S. Application Data

(60) Provisional application No. 60/089,365, filed on Jun. 15, 1998.

(51) Int. Cl.[7] .................................................. A61B 5/00
(52) U.S. Cl. ........................ 600/426; 600/414; 600/417; 600/429; 606/130
(58) Field of Search ................................. 600/414, 415, 600/417, 426, 429; 378/205, 206; 606/130

(56) References Cited

U.S. PATENT DOCUMENTS

| | | | | |
|---|---|---|---|---|
| 4,293,771 A | * | 10/1981 | Lescrenier | 250/491 |
| 4,426,726 A | * | 1/1984 | Cheetham | 378/206 |
| 4,836,671 A | * | 6/1989 | Bautista | 378/206 |
| 5,517,990 A | * | 5/1996 | Kalfas et al. | 600/414 |
| 5,590,655 A | * | 1/1997 | Hussman | 600/414 |
| 5,598,269 A | * | 1/1997 | Kitaevich et al. | 356/399 |
| 5,868,675 A | * | 2/1999 | Henrion et al. | 600/424 |
| 5,957,933 A | * | 9/1999 | Yanof et al. | 606/130 |
| 5,957,934 A | * | 9/1999 | Rapoport | 606/130 |
| 6,021,342 A | * | 2/2000 | Brabrand | 600/427 |
| 6,041,249 A | * | 3/2000 | Regn | 600/429 |
| 6,044,291 A | * | 3/2000 | Rockseisen | 600/429 |
| 6,064,904 A | * | 5/2000 | Yanof et al. | 600/414 |

* cited by examiner

Primary Examiner—Ruth S. Smith
(74) Attorney, Agent, or Firm—Hodgson Russ LLP (57) ABSTRACT

A targeting device defines a direction of approach to a subsurface target under guidance of imaging equipment such as a computer tomograph or a magnetic resonance imaging machine. The targeting device is positioned relative to the target in such a way that the optimal direction of approach avoiding vital internal structures can be selected by reference to the images displayed on the imagine equipment. The device projects a visible light beam, such as a laser beam, on a region of a patient, indicating the point of entry and the angle of approach to the subsurface target.

53 Claims, 10 Drawing Sheets

Fig_3

Fig_4A

Fig_6

METHOD AND DEVICE FOR DETERMINING ACCESS TO A SUBSURFACE TARGET

CROSS-REFERENCE TO A RELATED APPLICATION

Applicants hereby claim priority on earlier filed provisional patent application Ser. No. 60/089,365 filed Jun. 15, 1998, which is incorporated herein by reference.

BACKGROUND OF THE INVENTION

1. Field of the Invention

This invention relates generally to determining the location of and the direction of access to a target identified by an imaging technique, such as computer tomography or magnetic resonance imaging. More specifically, the invention relates to a device and method for determining the optimal path to a subsurface target by correlating the optimal path to an image of a subsurface target defined by images of markers in a CT or MRI image and a direction of a visible light beam aimed at the target.

2. Background Art

Guidance systems using visible light to illuminate the direction of approach to a target located in a patient were known in the past. When a guidance system was used together with an imaging machine, such as a computer tomograph or an MRI, it was known to use one or more markers to help determine the position of a targeted area relative to the imaging equipment. For example, U.S. Pat. No. 5,769,861 to Vilsmeier discloses a method of localizing an instrument in which internal markers implanted in the body of a patient and secured to the patient's skull or skeleton are utilized to determine an internal reference system for performing CT or MRI imaging. Fixedly connected to the internal markers are external markers serving as an external reference frame for determining the orientation of the external markers relative to the internal markers in an imaging machine. Additionally, in order to position an instrument relative to the two frames defined by internal and external markers, the instrument itself must be provided with at least two markers to determine the inclination of the instrument. Clearly, it would be desirable to provide a method for positioning an instrument in an imaging machine without having to use two sets of marker frames, one of which has to be implanted in the patient.

A light guiding system generating a laser beam for use with a CT scanner is described in the article "Laser Guidance System for CT-guided Procedures", Radiology, January 1995, v.194. No.5, pp. 282–284. In that article a protractor supporting a laser beam was mounted on a horizontal or vertical rail affixed to a CT gantry. The laser beam could be rotated about the center of the protractor. The method of using the protractor with the laser beam to indicate the direction of approach to a target consisted of the following steps. A number of CT images of the targeted region was obtained and the point of entry on the skin and the target point were chosen on a CT image. The angle of incidence to the path between the target and the entry point was then chosen. Then the point of entry was marked by placing a radio-opaque marker on the patient's skin. After that the patient was moved out of the scanning plane and the protractor was inclined to match the angle of incidence and moved along the rail until the laser beam was coincident with the entry point on the skin.

The system and method described in the foregoing article have a significant disadvantage in that they allow only an approximate visual determination of the entry point and access path to the target based on a CT image without referencing that path to the direction of the laser beam at the time the CT image is taken. Moreover, after the radio-opaque marker is placed on the patient's skin, additional imaging is necessary to ensure the proper placing of the marker on the entry point of the skin. Accordingly, it would be advantageous to have a system and method of target localization which would allow to select the point of entry and angle of approach to a target, mark that point on the patient's skin and simultaneously identify the direction of approach to the target with a light beam at the time imaging is performed. It would be even more advantageous to be able to identify various paths of accessing the target during one imaging procedure without having to repeat imaging to assess suitability of alternative paths.

SUMMARY OF THE INVENTION

It is, therefore, an object of the present invention to provide a system for use with imaging equipment wherein markers are used to correlate the point of entry and the angle of approach to a subsurface target in a three-dimensional patient space to those in the image of the patient displayed on the monitor of the imaging equipment.

Another object of the present invention is to provide a target localization system which has as many degrees of freedom as the image plane of an imaging machine. Such a system is advantageous in that it determines the optimal path to a target which is difficult to localize, the determination being made by following the motion of the image plane. Use of the system will not require to reposition the patient in order to perform additional imaging and determine the path to the target.

It is yet another object of the present invention to have a system which provides for translational and rotational motion of the visible light beam in a targeting system in order to increase the precision of target localization and determination of the preferred position of the target relative to the system and of the direction of access to the target.

It is also another object of the present invention to provide a method of determining and identifying a path to a subsurface target, wherein markers are used to determine the path with the help of an imaging machine and at the same time to define the line along which a visible light beam is directed as a guide for an instrument.

The system of the present invention comprises a radiolucent support structure such as a frame assembly positioned within the field of a CT scanner or another imaging machine. Suitable drive means such as a gear assembly can rotate the frame assembly about its axis of rotation. Two markers are attached to the frame assembly at opposite locations, i.e. 180 degrees apart. Markers used for x-ray imaging, such as CT scanning, are radio-opaque. Markers suitable for use in magnetic resonance imaging procedures are non-ferromagnetic, so they don't interfere with the MRI data gathering process. A term "fiducials" is used to represent markers suitable for a particular type of imaging. For example, "fiducials" can represent radio-opaque markers for CT scanning, or non-ferromagnetic markers that can be imaged with MRI. It is also understood that there exist fiducials that are both radio-opaque and non-ferromagnetic, which are, therefore, suitable for both CT and MRI imaging. Markers of that kind are manufactured, for example, by BRAIN LAB in the United States. In the description of the present invention the term "fiducials" is used to refer to either type of the markers or to the BRAIN LAB type of markers, depending on what type is better suitable for a particular imaging procedure.

A visible light source, either distant or attached to the frame, generates a light beam which is directed along the path between the two fiducials either by a radiolucent mirror or by the light source itself. The frame assembly can be positioned using x,y,z translation stages such that the coordinates of its center are localized on the subsurface target. In such a configuration a visible light beam always points toward the target as the visible light source is rotated by the frame assembly around the patient.

When the frame assembly is positioned in the image plane of a CT scanner and the patient's anatomy is imaged, the images of two fiducials will appear in the image of the anatomy displayed by the monitor of the scanner. A computer generated line between the two fiducial images will intercept certain regions of the patient's anatomy and, at the same time, will correspond to the line along which the light beam is directed in the frame assembly of the present invention. A CT operator can rotate the frame assembly up to 360 degrees to position the fiducials anywhere around the patient and, therefore, to position the fiducial images anywhere around the image of the patient's anatomy.

In such a frame assembly a visible light beam is directed on the patient along the line which is represented by the line displayed on the monitor of the scanner. The light beam indicates the point of entry on the patient's skin and defines the angle of approach to the target corresponding to the point of entry and the angle of the line defined by the two fiducial images on the scanner monitor. By measuring the distance between the skin and the intended target in the CT image, the depth of penetration of the instrument can be determined.

During an imaging procedure the frame assembly is positioned such that the fiducials lie in the image plane of the imaging machine. An image of the target is displayed on the monitor together with the images of the fiducials. A line drawn between the two fiducial images intercepts the target image, thus indicating the point of entry and axis of approach to the target in the patient space. To be able to choose the preferred path to the target, the operator of the imaging machine may remotely reposition the fiducials relative to the frame assembly, or change the position of the frame assembly itself. Once the preferred path to the target is selected, the imaging machine can be turned off. A visible light beam illuminating the selected preferred path to the subsurface target will guide a surgeon performing an invasive medical procedure without exposing the surgeon and the patient to excessive radiation or magnetic fields.

These and other objects and advantages of the present invention will become increasingly more apparent to those skilled in the art by reference to the following description and to the accompanied drawings.

DETAILED DESCRIPTION OF THE PREFERRED EMBODIMENT

Figure 1:
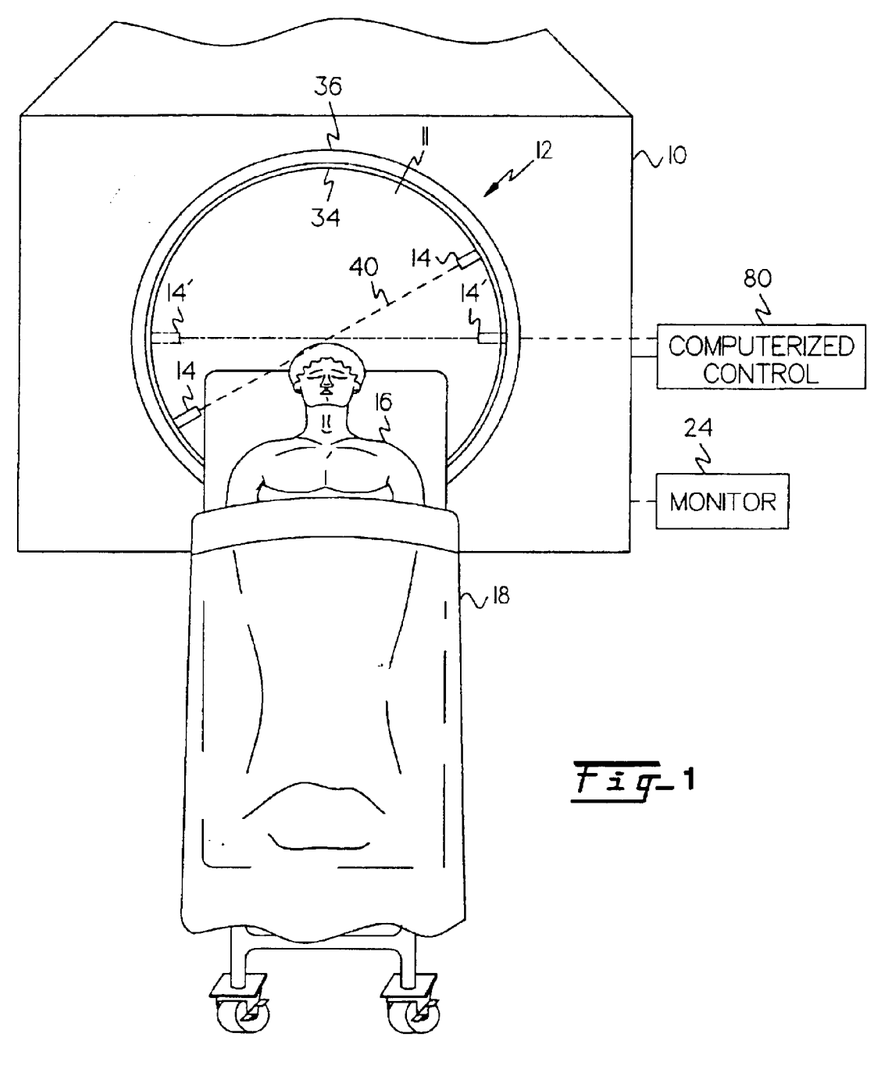
FIG. 1 is a schematic representation of the frame assembly of the present invention in the tunnel of a CT scanner.

Turning now to FIG. 1, the present invention comprises a support structure in the form of a radiolucent frame assembly 12 positioned in the image plane of imaging equipment 10, such as a CT scanner or a magnetic resonance imaging machine. Frame assembly 12 comprises an outer support member and an inner support member which is freely moveable with respect to the outer support member. In the preferred embodiment of the present invention, illustrated in detail in FIGS. 4A–4C, both the outer and the inner support members are in the form of rings 36 and 34 which are concentrical and coplanar. Outer ring 36 defines a track 35 in which inner ring 34 is rotated by a motor gear assembly via a remote control device.

The diameter of outer radiolucent ring 36 preferably is such that it can be positioned within the image field of a CT scanner or an MRI machine. At the same time the diameter of inner ring 34 has to be large enough to accommodate the body of a patient 16 inside frame assembly 12. Furthermore, outer ring 36 must be of a diameter to allow for movements of frame assembly 12 inside a scanner or magnetic imaging equipment when positioning the frame assembly to encompass a particular region of the patient's anatomy.

Figure 2:
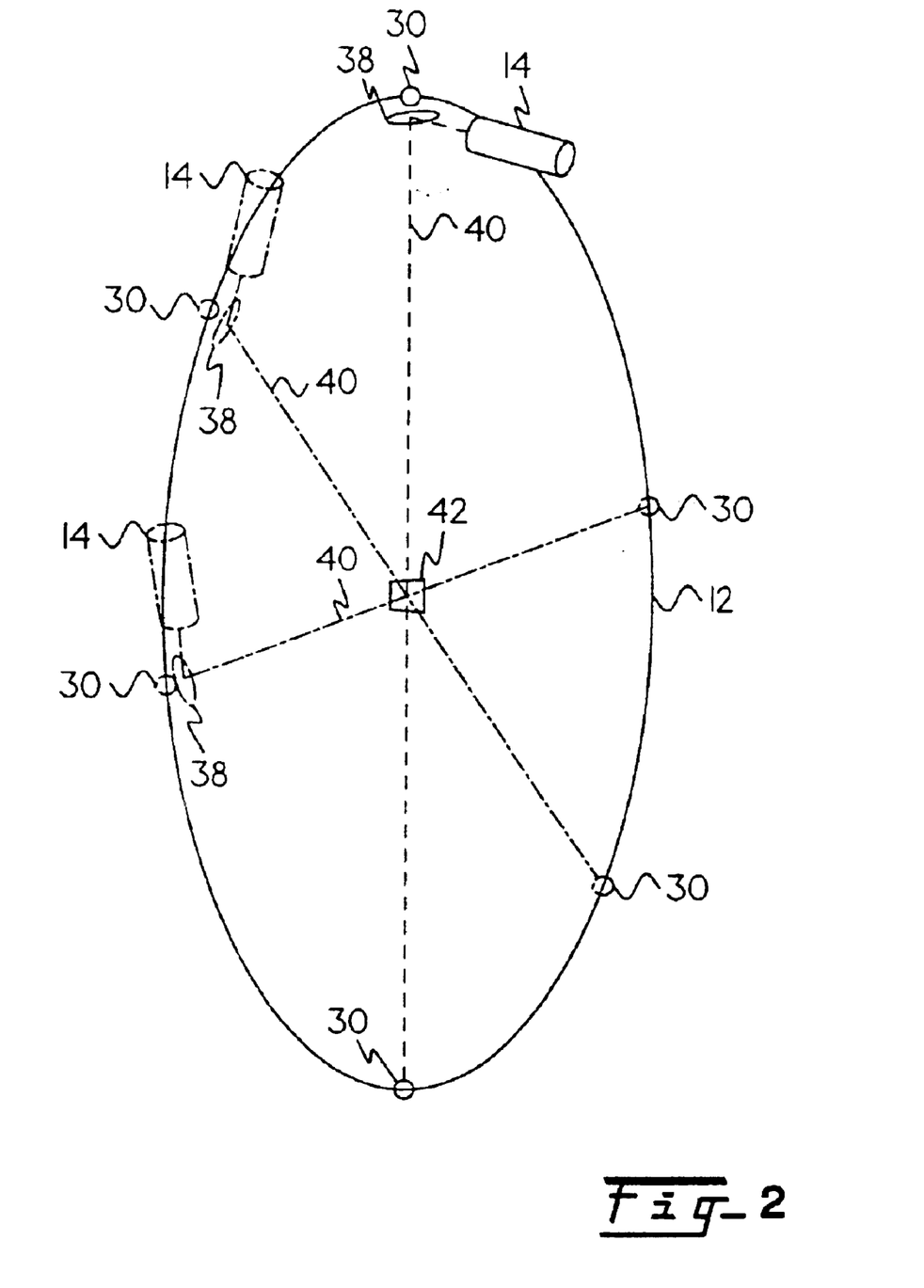
FIG. 2 is a schematic representation of the elements of the frame assembly of the present invention.

Inner ring 34 carries a plurality of spaced apart fiducials. In the preferred embodiment of the present invention, illustrated in FIG. 2, the inner ring carries two fiducials 30 situated at the opposite ends of the diameter of the inner ring (i.e. 180 degrees apart). Additionally, frame assembly 12 carries a radiolucent mirror 38 and at least one visible light source 14 which generates a visible light beam 40, represented by dashed line in FIGS. 1–3 and directs it to the mirror. The mirror is positioned to reflect the visible light beam 40 from light source 14 and to direct the reflected beam along the line defined by the two fiducials. It is contemplated by the present invention that frame assembly 12 can carry two or more visible light sources. For example, the frame assembly can carry two oppositely spaced visible light sources 14 serving as fiducials at the same time. In such a design of the frame assembly one or both visible light sources generate visible light beams directed toward each other along the diameter line defined by the two sources. Any collimated visible light beam will illuminate the line, but in the preferred embodiment of the present invention the visible light beam is a laser beam.

The frame assembly 12 is manufactured of materials that do not interfere or otherwise degrade the imaging capability of a CT scanner or an MRI machine. A frame assembly 12 which is intended for use with MRI imaging equipment should not contain ferromagnetic materials that can interfere with the accuracy of the MRI data gathering process. The material used for manufacturing the fiducials 30 can be anything that is not transparent to x-rays for CT imaging, for example, lead or gadolinium, or a material that can be imaged with MRI, such as gadolinium. The materials of which the radiolucent mirror 38 is made are transparent to x-rays. For example, the mirror can be made of plastic covered with Ag to reflect the visible light beam. A mirror made of thin Al will also be invisible in x-rays, but will serve as a reflector for visible light. Other materials with similar properties can be used to manufacture the mirror, as required by a particular application.

Figure 4A:
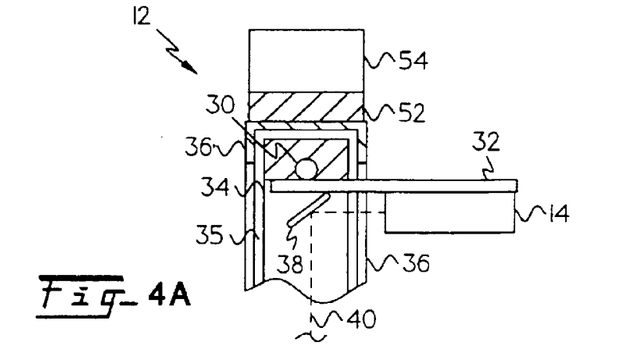
FIG. 4A is a cross sectional view taken about on line 4A—4A in FIG. 3 and showing a fiducial, radiolucent mirror and a visible light source mounted on the assembly.
Figure 4B:
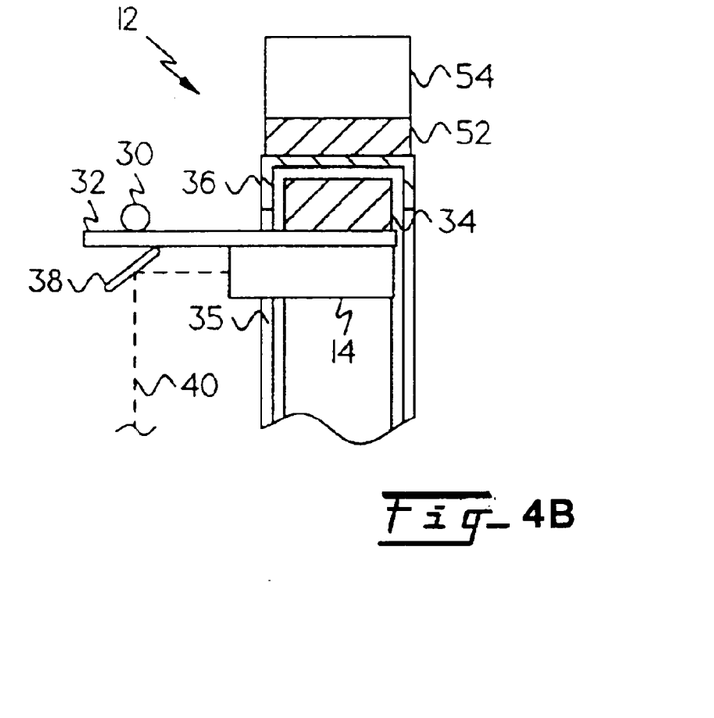
FIG. 4B is a cross sectional view similar to FIG. 4A and showing another embodiment of a frame assembly.
Figure 4C:
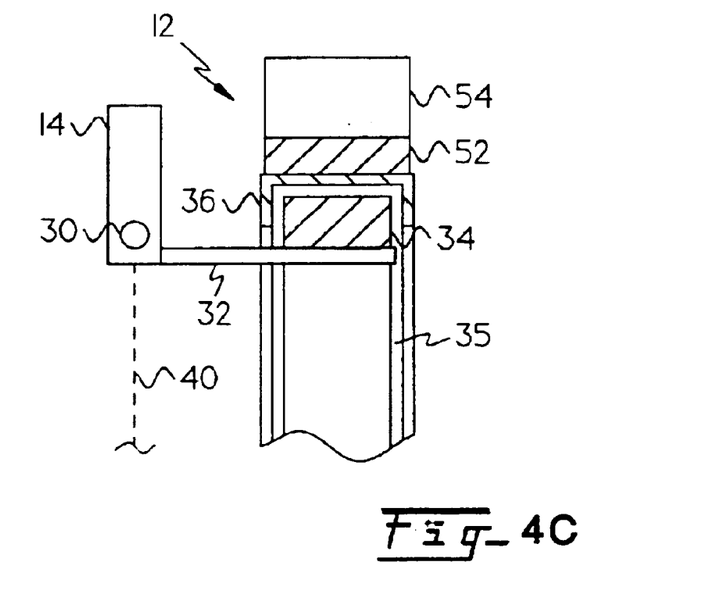
FIG. 4C is a cross sectional view similar to FIG. 4A and showing yet another embodiment of a frame assembly.

All other components of the frame assembly that are located in the image plane of an imaging device are x-ray transparent and, therefore, not seen in the resulting image of the patient's anatomy. As FIGS. 4A–4C illustrate, frame assembly 12 is implemented in several embodiments. FIG. 4A shows a brace 32, one end of which supported by inner ring 34 rotating in a track 35 of outer ring 36. Fiducial 30, which is attached to inner ring 34, rotates together with the inner ring. Attached to the same end of brace 32 is a radio-lucent mirror 38 which receives visible light beam 40 from visible light source 14 and reflects it along the diameter of inner ring 34. In FIG. 4A visible light source 14 is situated at the other end of brace 32. In that embodiment both outer ring 36 and inner ring 34 are made of a material that is x-ray transparent, or does not interfere with formation of an image in an MRI machine, such as plastic.

A different embodiment of the frame assembly of the present invention is shown in FIG. 4B, where outer ring 36 and inner ring 34 are attached to the same end of brace 32 as visible light source 14. The other end of brace 32 carries fiducial 30 and radio-lucent mirror 38, both of which are in the image plane of a CT scanner. In this embodiment both rings 34, 36 are removed from the image plane, thus, reducing the risks of their interfering with formation of the image and degrading the image quality.

In yet another embodiment of the frame assembly 12 of the present invention, illustrated in FIG. 4C, one end of brace 32 supports visible light source 14 which carries fiducial 30. The other end of brace 32 is carried by inner ring 34 which rotates brace 32 in track 35 of outer ring 36. In such an embodiment visible light source 14 generates visible light beam 40 and directs it along the diameter of inner ring 34, therefore eliminating the need to use a radio-lucent mirror.

In order to reduce the possibility of degrading the quality of a CT or MRI image by the materials used to manufacture the visible light source, the present invention contemplates a frame assembly wherein the source is located away from the image plane. In that case the visible light beam is transmitted to the image plane via fiberoptics or other light conductors.

Figure 3:
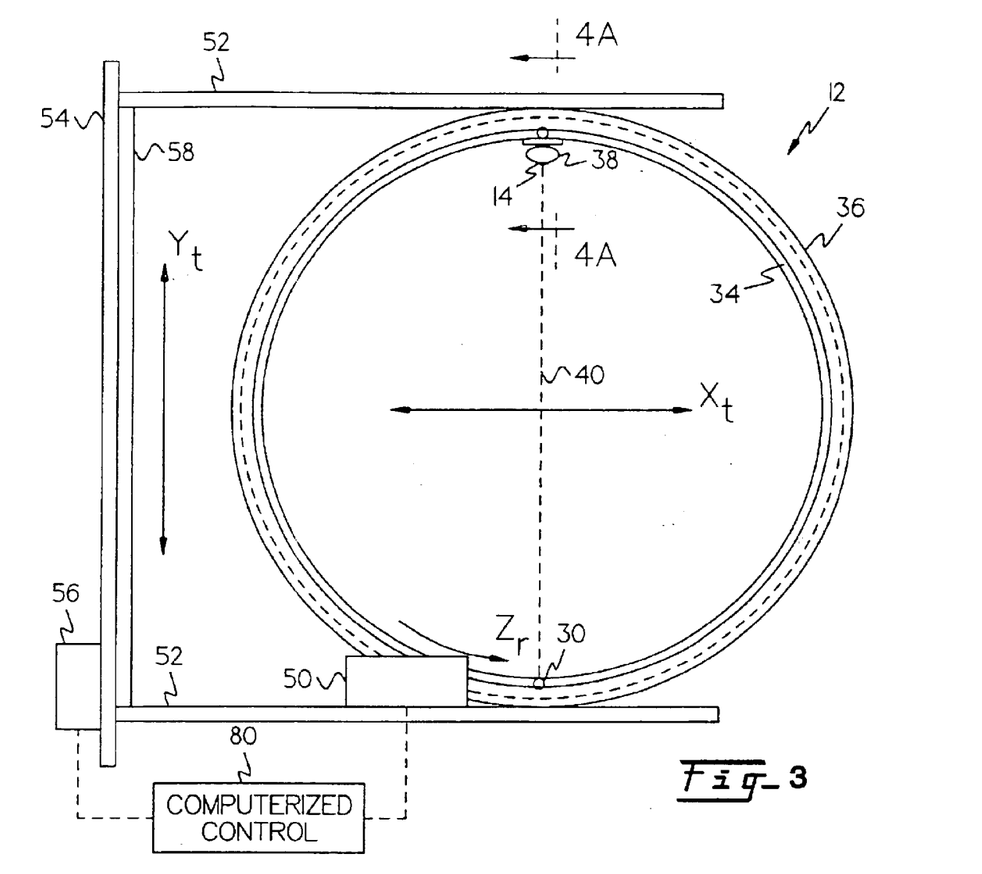
FIG. 3 is an illustration of an X-translational, Y-translational and Z-rotational motion of the frame assembly of the present invention.
Figure 5:
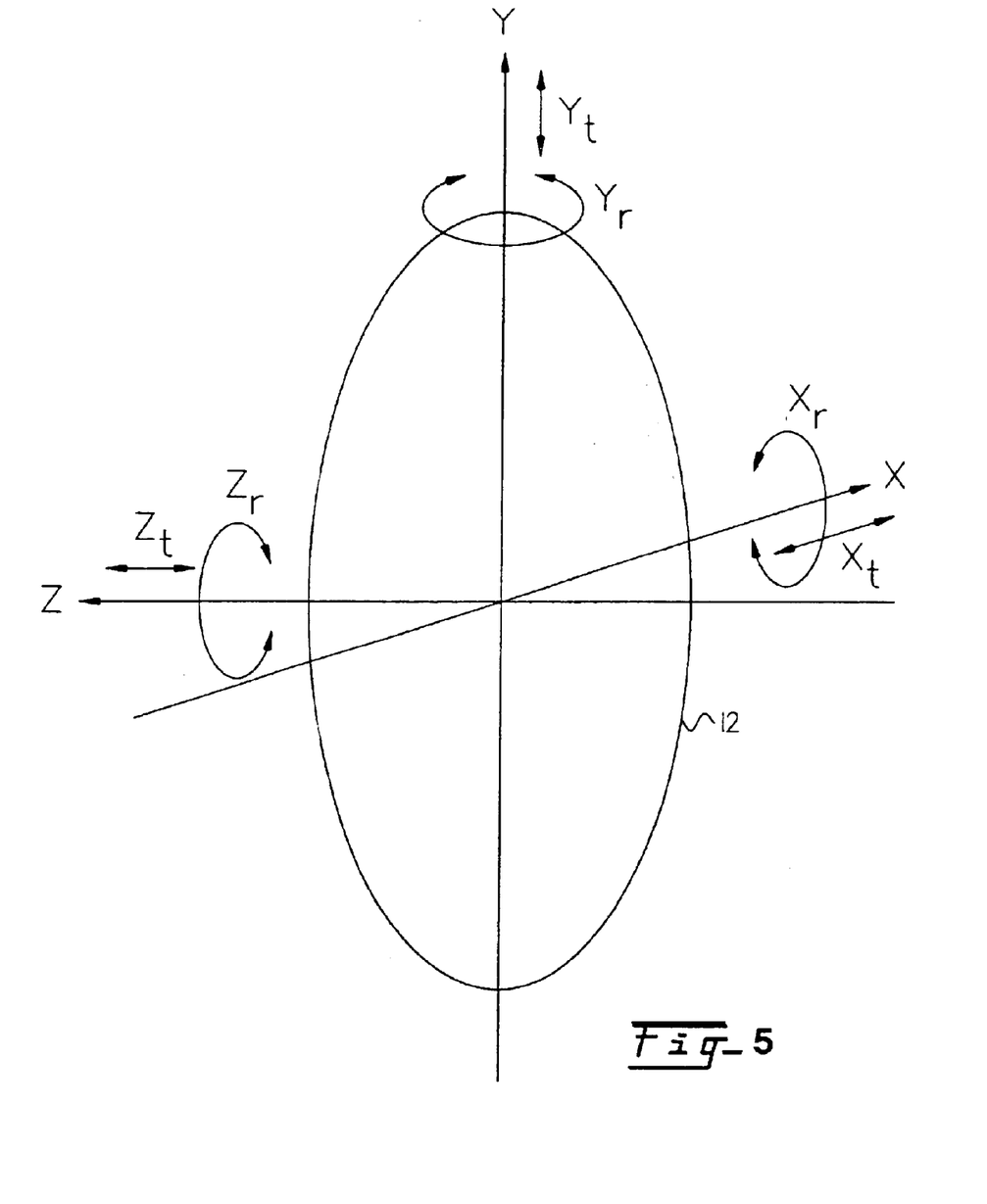
FIG. 5 is a schematic illustration of degrees of freedom of the frame assembly of the present invention.

If the image plane is fixed with respect to imaging equipment, the frame assembly possesses at least three degrees of freedom: two translational, $X_t$ and $Y_t$, and one rotational $Z_r$. Translational degrees of freedom allow the frame to move along X and Y directions within the image plane, as shown in FIG. 5. The rotational degree of freedom allows the frame to rotate around the Z axis, which is perpendicular to the image plane. Furthermore, as shown in FIG. 3 there are two horizontal guides 52 which provide for translational motion $X_t$ of frame assembly 12 along the X axis. A vertical support pole 54 carries a slide 58 which provides for translational motion $Y_t$ of the frame assembly along the Y axis. An X-Y translational stage drive assembly 56 moves frame assembly 12 along the X and Y axes. A gear assembly 50 rotates the inner ring (not shown) of frame assembly 12 around the Z axis.

However, when the image plane has its own degrees of freedom (in other words, it can move with respect to the imaging equipment), as is the case with some types of such equipment, then the frame assembly possesses additional degrees of freedom which allow the frame to move with the image plane: a translational along the Z axis, a rotational around the X axis and a rotational around the Y axis. As shown in FIG. 5, which illustrates the maximum number of degrees of freedom of the frame assembly of the present invention, in addition to degrees of freedom $Y_t, X_t,$ and $Z_r$, frame assembly 12 has a translational degree $Z_t$ and rotational degrees $Y_r$ and $X_r$.

Operation of the frame assembly of the present invention can be illustrated by an example that describes a computer tomographic localization of a subsurface target inside a patient with the help of a CT image. During a computer tomography procedure frame assembly 12 is inserted into a tunnel 11 of CT scanner 10 shown in FIG. 1, so that the fiducial lie in the image plane, but the gear assembly and the visible light source are located away from the image plane. In the preferred embodiment of the present invention frame assembly 12 is coupled to a table 18 on which a patient 16 is positioned, so the frame assembly can move in and out of CT scanner 10 together with table 18 without distorting the positional alignment of the elements of the assembly with respect to the patient. Such coupling can be provided, for example, by an arrangement such as that shown in FIG. 3.

Figure 6:
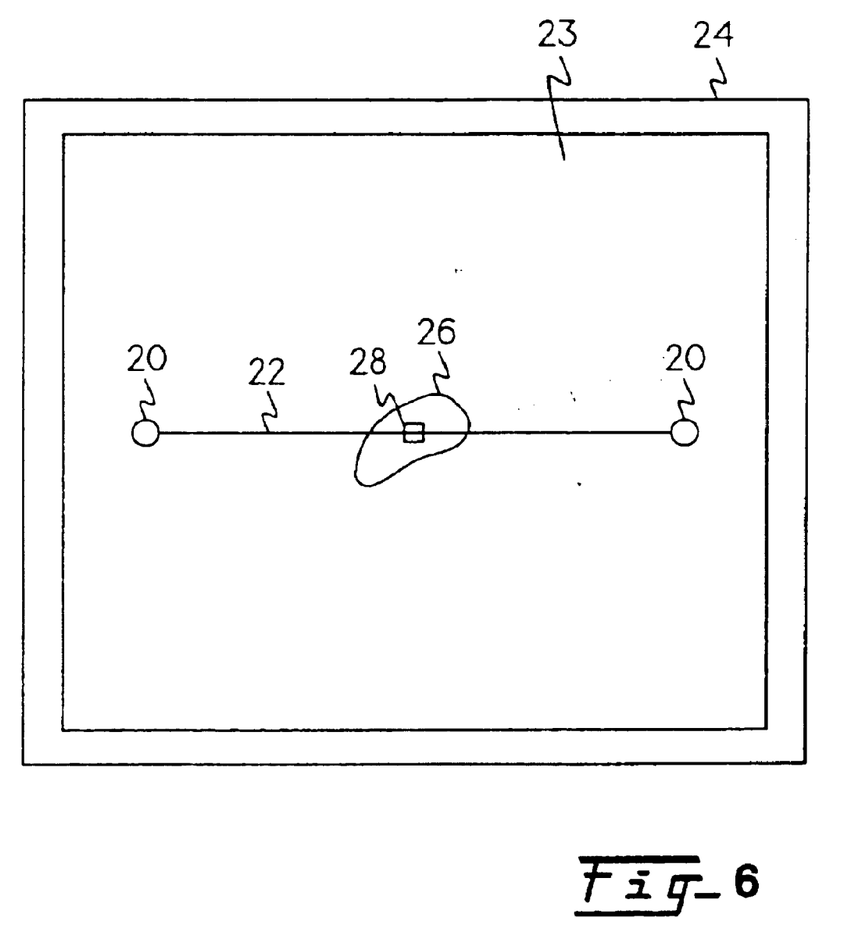
FIG. 6 is an illustration of images of fiducials defining a line intercepting an image of patient's anatomy.

When the patient's anatomy is imaged by the CT scanner with the fiducials in the image plane, images 20 of the fiducials are seen on a CT image 23 displayed on monitor 24 of the scanner, depicted in FIG. 6. A target line 22 between fiducial images 20 intercepting an anatomy image 26 of a subsurface target displayed on the video monitor 24 of the scanner, as illustrated in FIG. 6, is generated by the software running on the CT scanner. The operator of the CT scanner can use a remote control device to rotate the inner ring 34 of the frame assembly 12 to position the fiducials anywhere along the circumference of the inner ring. The new positions of fiducials 30, mirror 38 and visible light source 14 are shown in broken lines in FIG. 2. In FIG. 1 the new positions of two visible light sources 14 are shown as 14. Repeating the CT image after rotating the inner ring and repositioning fiducials displays images 20 of the fiducials in CT image 23 in their new location relative to the patient, as shown in broken lines in FIGS. 7A and 7B. Preferably, repositioning the fiducials is repeated as necessary until the target line intercepts the desired area of the patient's anatomy at a desired point and direction. It is also possible to practice the present invention with one fiducial attached to the frame assembly, in which case the second point defining the path to the target, such as, for example, the center of a circular or oval frame assembly, will be known and referenced in the imaging machine.

Figure 7A:
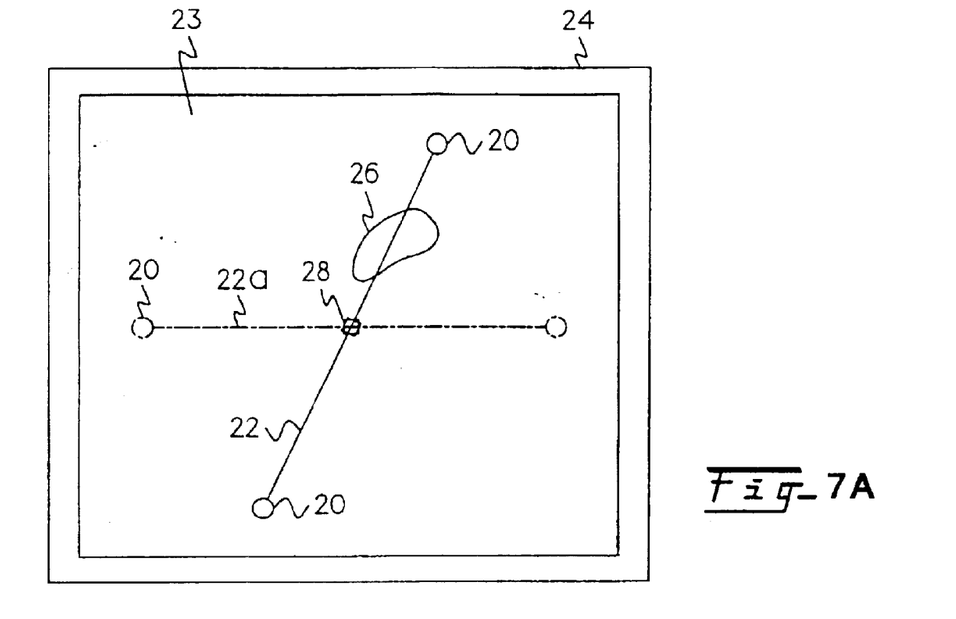
FIGS. 7A–7B are illustrations similar to FIG. 6 and providing schematic representations of images of patient's anatomy in different locations relative to fiducials.
Figure 7B:
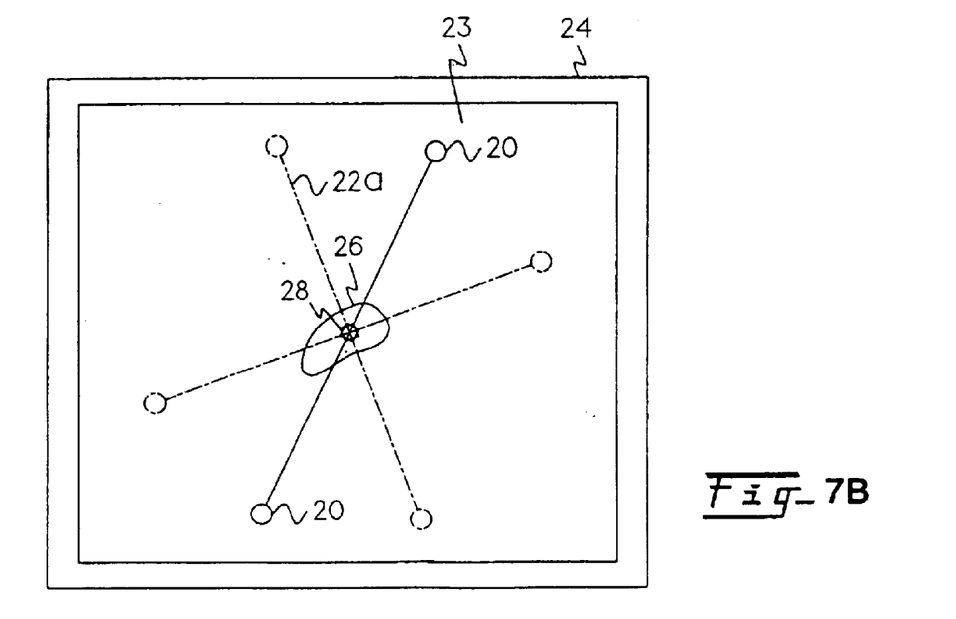
Figure 11:
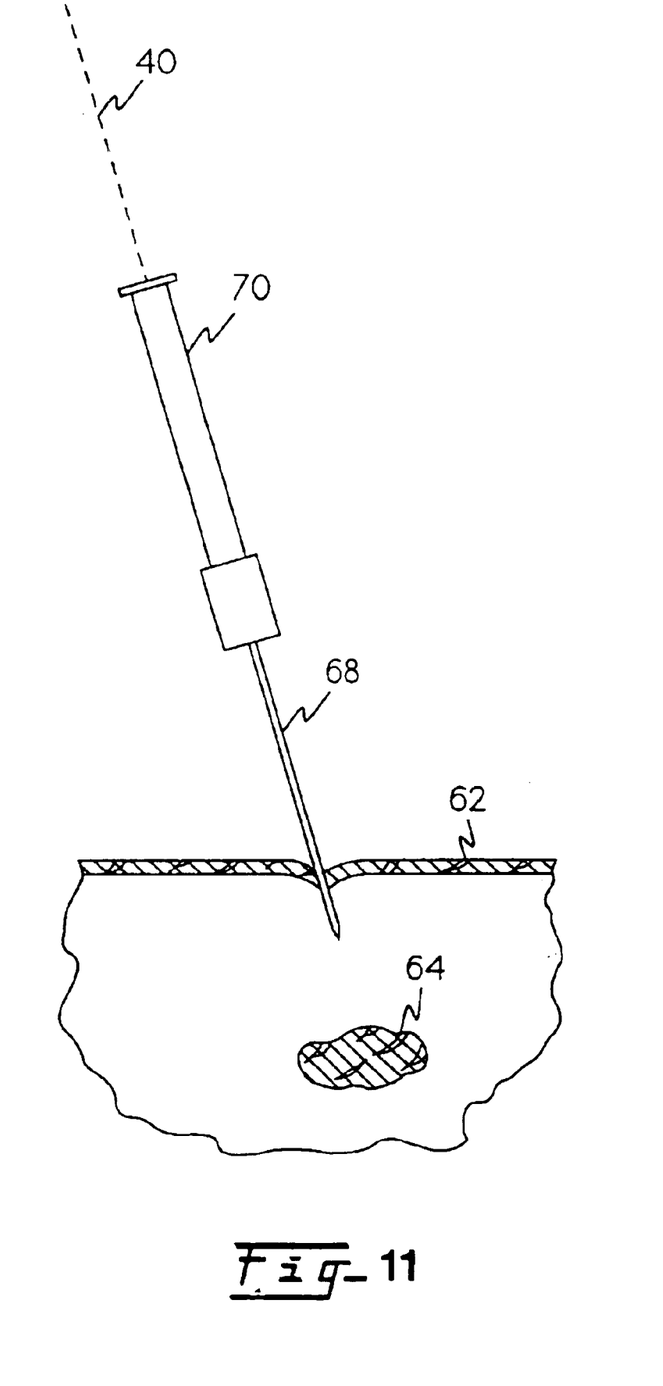
FIG. 11 is an illustration of a direction of approach to a subsurface target illuminated by the light beam to guide an invasive instrument.

Proper positioning of target line 22 relative to anatomy image 26 in CT image 23, as in FIG. 6 or 7A–7B, corresponds to the direction of visible light beam 40 in frame assembly 12 defined by two fiducials 30. Target line 22 in CT image 23 corresponds to the direction of visible light beam 40 directed at a patient. Therefore, visible light beam 40 indicates and uniquely defines the point of entry and the angle of approach to the subsurface target in the patient. As illustrated in FIG. 11, an invasive instrument 70 comprising a needle or an electrode 68 positioned colinearly with visible light beam 40 and advanced into the patient will intercept such points and regions in the patient as are intercepted by target line 22 in CT image 23. Moreover, by measuring the distance from skin 62 to a subsurface target 64 with the help of CT image 23, the depth to which invasive instrument 70 should be advanced into the patient in order to reach subsurface target 64 will be known.

Once the direction of advancement of invasive instrument 60 into the patient is defined and illuminated by the visible light beam 40, a CT scanner or an MRI machine can be turned off before the beginning of the invasive procedure. Turning the imaging equipment off minimizes the exposure of the patient and medical personnel to x-rays and strong magnetic fields without sacrificing accuracy and precision of the invasive procedure guided by the visible light beam in the frame assembly of the present invention.

It may happen that a particular direction of target line 22 intercepting anatomy image 26 in CT image 23 is undesirable, because invasive instrument 60 advancing along such a direction may damage vital organs or blood vessels disposed between skin 62 of the patient and subsurface target 64. In order to find a suitable direction of target line 22 which avoids vital organs, inner ring 34 is rotated to reposition target line 22 and, therefore, the line defined by two fiducials in frame assembly 12. Unless anatomy image 26 is located in the center 28 of target line 22, rotation of inner ring 34 will reposition target line 22 in such a way that the target line will not be intercepting anatomy image 26 anymore, as illustrated in FIG. 7A. To overcome this difficulty, the method of the present invention provides for positioning anatomy image 26 in center 28 of target line 22 in CT image 23, then rotating inner ring 34 about center 28 until a suitable point of entry and angle of approach to anatomy image 26 are identified, as illustrated in FIG. 7B. To accomplish positioning of anatomy image 26 in center 28 of target line 22, X-Y translational stage drive assembly 56 in FIG. 3 allows motion of the frame assembly in X and Y directions until the center of inner ring 34 coincides with the coordinates of the subsurface target. When that happens, center 28 of target line 22 will coincide with anatomy image 26 in CT image 23, as illustrated in FIG. 7B. The amount of the necessary X and Y displacement is measured based on CT image 23 on monitor 24 by the computer which then calculates the required displacement.

Figure 8:
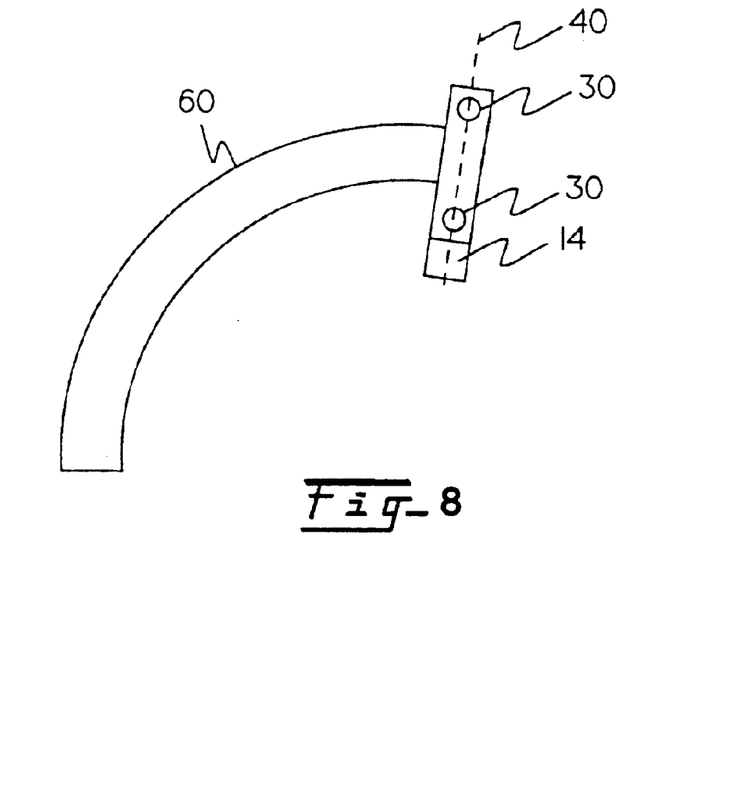
FIG. 8 is a front view of an arc embodiment of the present invention.
Figure 9A:
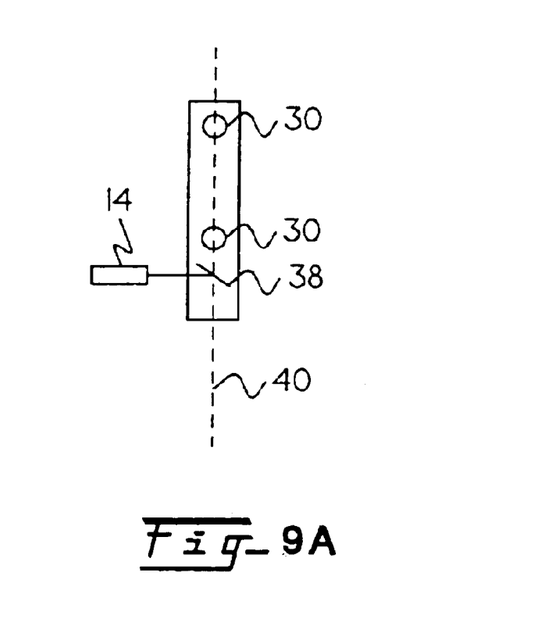
FIG. 9A is a side view of an arc embodiment similar to that of FIG. 8, but wherein fiducials are located in the image plane on the same side of the patient and a visible light source is located outside the image plane.
Figure 9B:
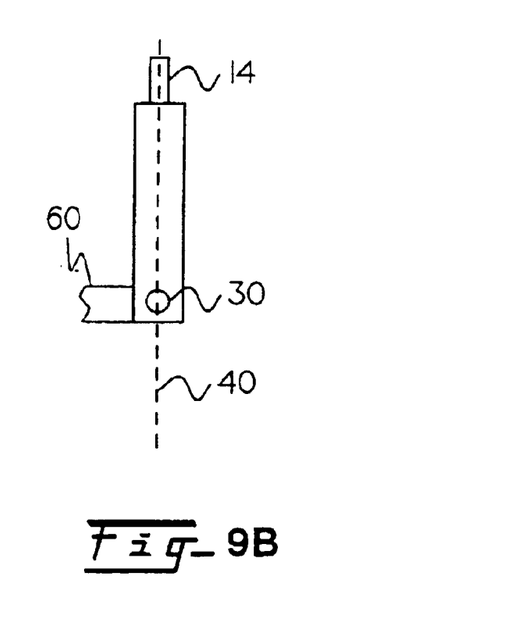
FIG. 9B is a side view of an arc embodiment similar to that of FIG. 8 but wherein a light source serves as a fiducial located in an image plane.
Figure 10:
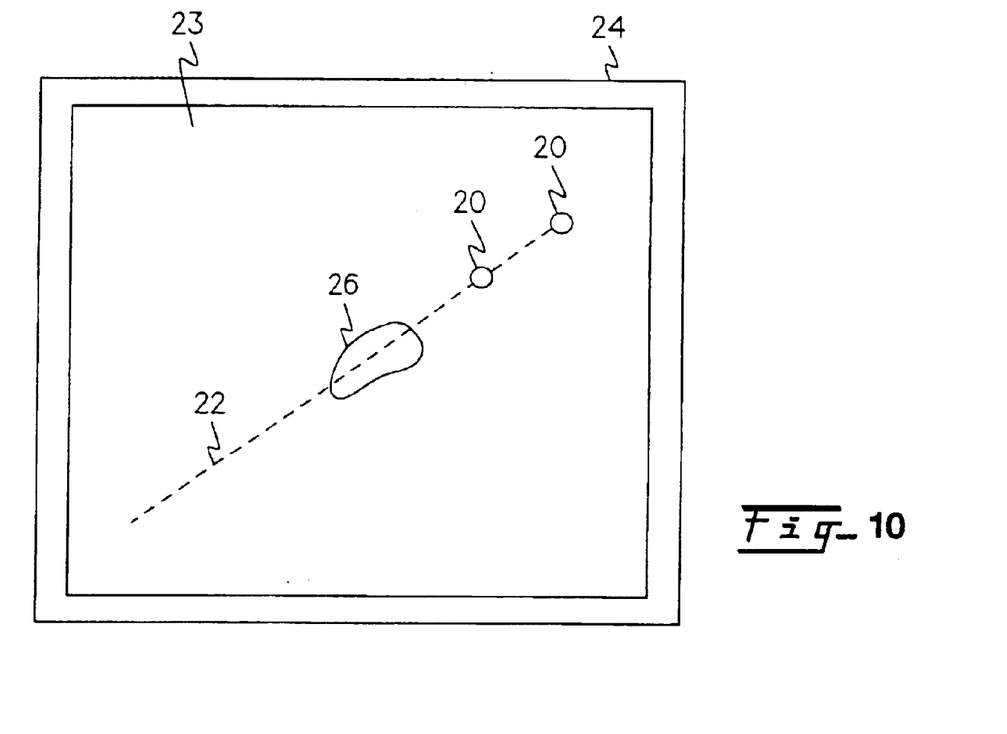
FIG. 10 is a schematic representation of an image of patient's anatomy together with images of fiducials.

An alternate embodiment of the frame assembly of the present invention is illustrated in FIGS. 8–9. In that embodiment a frame assembly is reduced to an arc 60 carrying fiducials 30 situated in the image plane of an imaging machine. Depending on a particular imaging machine, the use of arc 60 may be advantageous over the use of a circular or oval frame assembly. As shown in FIGS. 8–9, fiducials define a line along which a visible light beam 40 is directed by radiolucent mirror 38. Visible light beam 40 is generated by a visible light source 14. Images 20 of fiducials 30 define a line intercepting a target image 26 on monitor 24 of the imaging machine, as illustrated in FIG. 10. Arc 60 possesses various degrees of freedom allowing it to move rotationally or translationally facilitating selection of the optimal path to the subsurface target. Visible light source 14 can be situated apart from the image plane, as shown in FIG. 9A, or in the image plane, as shown in FIG. 9B. If light source 14 is situated in the image plane, it can also serve as one of the fiducials 30, eliminating the need for a separate second fiducial.

It should be readily apparent to anyone skilled in the art that various steps of the present invention can be performed, controlled and optimized by selecting appropriate settings and parameters and inputting them into a program or a number of programs that implement computer-integrated control 80 of the invention, as shown in FIGS. 1 and 3. It is therefore apparent that the present invention accomplishes its intended objects. While embodiments of the present invention have been described in detail, that is done for the purpose of illustration, not limitation.

What is claimed is:

1. An apparatus for defining a direction of approach to a subsurface target along a predetermined path comprising:
    imaging equipment having an image plane;
    a support structure carrying a plurality of fiducials defining the predetermined path relative to the support structure, the support structure having a size and shape locating the fiducials outwardly of the surface and defining an air gap between the fiducials and the surface and locating the fiducials in the image plane, the support structure being translationally and rotationally movable; and
    a visible light source generating a visible light beam traveling along the predetermined path and being indicative of a direction of approach to the subsurface target.

2. The apparatus of claim 1, wherein the support structure is radiolucent.

3. The apparatus of claim 1 further comprising a radiotransparent reflector for directing the visible light beam along the predetermined path.

4. The apparatus of claim 3, wherein the support structure is substantially circular.

5. The apparatus of claim 1, wherein the support structure is substantially circular.

6. The apparatus of claim 5, wherein the predetermined path is defined along the diameter of the support structure.

7. The apparatus of claim 5, wherein a displacement of the support structure relative to the subsurface target places the subsurface target in the center of the diameter of the support structure.

8. The apparatus of claim 1, wherein the visible light source serves as one of the fiducials.

9. The apparatus of claim 1, wherein the visible light source is mounted on the support structure.

10. The apparatus of claim 1, wherein the visible light beam travels from the visible light source to the predetermined path through a light conductor.

11. The apparatus of claim 1, wherein the support structure comprises two oppositely spaced fiducials.

12. The apparatus of claim 1, wherein a displacement of the fiducials relative to the subsurface target alters the predetermined path to the subsurface target.

13. The apparatus of claim 1, wherein the visible light beam is a laser beam.

14. The apparatus of claim 1, wherein the fiducials are radio-opaque.

15. The apparatus of claim 1, wherein the fiducials are non-ferromagnetic.

16. A system for defining a direction of approach to a subsurface target by illuminating a predetermined path with a visible light beam, the system comprising:

an imaging machine having an image plane, the image plane having a plurality of degrees of freedom;

a support structure having at least one rotational and at least two translational degrees of freedom;

at least two fiducials mounted on the support structure and the fiducials being situated in the image plane, the support structure having a size and shape locating the fiducials outwardly of the surface and defining an air gap between the fiducials and the surface; and a visible light source generating the visible light beam traveling along the predetermined path and illuminating the path as a direction of approach to the subsurface target.

17. The system of claim 16, wherein the imaging machine is a computer tomograph or a magnetic resonance imaging machine.

18. The system of claim 16, wherein the support structure has as many degrees of freedom as the image plane of the imaging machine.

19. The system of claim 16, wherein the support structure is substantially circular.

20. The system of claim 19, wherein the path is defined along the diameter of the support structure.

21. The system of claim 16 further comprising a radiotransparent reflector coupled to the support structure for directing the visible light beam along the path.

22. The system of claim 16, wherein the visible light beam is a laser beam.

23. The system of claim 16, wherein the visible light beam travels from the visible light source to the path through a light conductor.

24. The system of claim 16, wherein the fiducials are radio-opaque.

25. The system of claim 16, wherein the fiducials are non-ferromagnetic.

26. A system for defining a direction of approach to a subsurface target by illuminating a predetermined path with a visible light beam comprising:

an imaging machine having an image plane;

a support structure having a plurality of fiducials defining the predetermined path relative to the support structure, the support structure having a size and shape locating the fiducials outwardly of the surface and defining an air gap between the fiducials and the surface and locating the fiducials in the image plane, the support structure being translationally and rotationally movable;

a visible light source generating the visible light beam traveling along the path and illuminating the path as a direction of approach to the subsurface target; and a computer-based system for executing a set of procedures serving to select the predetermined path by determining an optimal path to the subsurface target.

27. The system of claim 26 further comprising a radiotransparent reflector coupled to the support structure for directing the visible light beam along the path.

28. The system of claim 26, wherein the imaging machine is a computer tomograph or a magnetic resonance imaging machine.

29. The system of claim 26, wherein the support structure comprises two oppositely spaced fiducials.

30. The system of claim 26, further comprising means for providing a displacement of the fiducials relative to the subsurface target to alter the path to the subsurface target, the displacement being calculated by the computer-based system.

31. The system of claim 26, wherein the support structure is substantially circular.

32. The system of claim 31, further comprising means for providing displacement of the support structure relative to the subsurface target to place the subsurface target in the center of the diameter of the support structure, the displacement being calculated by the computer-based system.

33. The system of claim 26, wherein the visible light beam is a laser beam.

34. The system of claim 26, wherein the fiducials are radio-opaque.

35. The system of claim 26, wherein the fiducials are non-ferromagnetic.

36. A method of determining a path to a subsurface target for use with imaging equipment having an image plane and an output device, the method comprising the steps of:

supporting a plurality of fiducials situated in the image plane, the fiducials being located outwardly of the surface in a manner defining an air gap between the fiducials and the surface and mounted to a support structure, the support structure being translationally and rotationally movable;

generating images of the plurality of fiducials in the output device;

observing positions of images of the plurality of fiducials in the output device; and utilizing the positions of the images of the plurality of fiducials to determine the path to the subsurface target.

37. The method of claim 36 further comprising repositioning the plurality of fiducials relative to the subsurface target, so that new positions of the images of the plurality of the fiducials can be utilized to identify another path to the subsurface target.

38. The method of claim 36 further comprising providing a visible light beam generated by a source, the visible light beam traveling along the path and illuminating the path as a direction of approach to the subsurface target.

39. The method according to claim 38, further comprising deactivating the imaging equipment while utilizing the visible light beam to approach the subsurface target.

40. The method of claim 38, wherein the visible light beam is a laser beam.

41. The method of claim 38, further comprising directing the visible light beam along the path by means of a radiotransparent reflector.

42. The method of claim 38, wherein the visible light beam travels from the source to the path through a light conductor.

43. The method of claim 36, wherein two oppositely spaced fiducials are situated in the image plane.

44. The method of claim 36, wherein the fiducials are radio-opaque.

45. The method of claim 36, wherein the fiducials are non-ferromagnetic.

46. A method of selecting a desired location of a subsurface target in an imaging machine having an image plane and having an output device for use with an apparatus comprising a plurality of fiducials carried by a support structure, the support structure being translationally and rotationally movable, wherein the method comprises the steps of:

positioning the support structure to locate the fiducials outwardly of the surface in a manner defining an air gap between the fiducials and the surface and to locate the fiducials in the image plane;

positioning the subsurface target relative to the apparatus in the imaging machine such a way that an image of the subsurface target and images of the plurality of fiducials can be observed on the output device and a location of the image of the subsurface target relative to the images of fiducials can be determined; and repositioning the plurality of fiducials so that a new location of the image of the subsurface target relative to the images of the plurality of fiducials is the desired location.

47. The method of claim 46, wherein the support structure is substantially circular.

48. The method of claim 46, wherein the support structure comprises two oppositely spaced fiducials.

49. The method of claim 48, wherein the desired location of the image of the subsurface target is in about the center of a line between the fiducials.

50. The method of claim 46 further comprising executing a set of procedures on a computer-based system to implement computer-integrated control of positioning the subsurface target relative to the apparatus, and repositioning the plurality of fiducials.

51. A method of positioning an apparatus for determining a direction of approach to a subsurface target in an imaging machine, the imaging machine comprising an image plane having a plurality of degrees of freedom, the method comprising the steps of:

providing a support structure having at least one rotational and at least two translational degrees of freedom;

providing at least two fiducials carried by the support structure;

positioning the support structure to locate the fiducials outwardly of the surface in a manner defining an air gap between the fiducials and the surface; and positioning the fiducials in the image plane of the imaging machine by moving the support structure along its at least one degree of freedom to generate an image of the fiducials for use in positioning the apparatus to determine the direction of approach to the subsurface target.

52. The method of claim 51, wherein the support structure has as many degrees of freedom as the image plane.

53. The method of claim 51 further comprising executing a set of procedures on a computer-based system to implement computer-integrated control of providing the support structure, providing at least two fiducials, and positioning the fiducials in the image plane.

* * * * *